United States Patent [19]

Logsdon et al.

[11] Patent Number: 4,876,402

[45] Date of Patent: Oct. 24, 1989

[54] IMPROVED ALDEHYDE HYDROGENATION PROCESS

[75] Inventors: John E. Logsdon, Houston; Richard A. Loke, Santa Fe, both of Tex.; Jay S. Merriam, Louisville, Ky.; Richard W. Voight, Houston, Tex.

[73] Assignee: Union Carbide Chemicals and Plastics Company Inc., Danbury, Conn.

[21] Appl. No.: 186,431

[22] Filed: Apr. 26, 1988

Related U.S. Application Data

[62] Division of Ser. No. 926,129, Nov. 3, 1986, Pat. No. 4,762,817.

[51] Int. Cl.$^4$ .............................................. C07C 29/14
[52] U.S. Cl. ................................................... 568/881
[58] Field of Search ....................... 568/881; 502/329

[56] References Cited

U.S. PATENT DOCUMENTS

| | | | |
|---|---|---|---|
| 1,797,426 | 3/1931 | Larson | 423/656 |
| 1,908,696 | 5/1933 | Dodge | 502/343 |
| 2,061,470 | 11/1936 | Larson | 518/713 |
| 2,079,414 | 5/1937 | Lazier | 568/814 |
| 2,517,223 | 8/1950 | Mantell | 502/338 |
| 2,549,416 | 4/1951 | Brooks | 568/881 |
| 2,552,300 | 5/1951 | Timm et al. | 568/487 |
| 2,658,921 | 11/1953 | Alheritiere | 568/462 |
| 2,835,706 | 5/1958 | Cordes | 568/403 |
| 3,197,418 | 7/1965 | Maebashi et al. | 252/454 |
| 3,303,001 | 2/1967 | Dienes | 23/213 |
| 3,431,311 | 3/1969 | Cooper et al. | 568/881 |
| 3,661,798 | 5/1972 | Cosyns et al. | 252/416 |
| 3,689,575 | 9/1972 | Tarhan | 568/840 |
| 3,790,505 | 2/1974 | Casey et al. | 252/463 |
| 3,798,178 | 3/1974 | Soderquist et al. | 252/468 |
| 3,927,120 | 12/1975 | Grane et al. | 568/814 |
| 3,927,121 | 12/1975 | Grane et al. | 568/814 |
| 4,048,196 | 9/1977 | Broecker et al. | 549/508 |
| 4,052,467 | 10/1977 | Mills et al. | 568/882 |
| 4,093,661 | 6/1978 | Trecker et al. | 568/319 |
| 4,111,847 | 9/1978 | Stiles | 252/463 |
| 4,113,662 | 9/1978 | Wall | 252/473 |
| 4,149,021 | 4/1979 | Wall | 568/864 |
| 4,186,112 | 1/1980 | Vogt et al. | 252/471 |
| 4,279,781 | 7/1981 | Dienes et al. | 252/463 |
| 4,283,581 | 8/1981 | Wilkes | 568/864 |
| 4,393,251 | 7/1983 | Broecker et al. | 568/811 |
| 4,451,657 | 5/1984 | Bradley et al. | 568/881 |
| 4,478,955 | 10/1984 | Pesa et al. | 518/713 |
| 4,489,048 | 12/1984 | Kuch | 423/416 |
| 4,564,643 | 1/1986 | Shibata et al. | 518/717 |
| 4,582,858 | 4/1986 | Shibata et al. | 518/713 |
| 4,598,061 | 7/1986 | Schneider et al. | 502/303 |

FOREIGN PATENT DOCUMENTS

| | | |
|---|---|---|
| 1137519 | 12/1982 | Canada . |
| 0008767 | 3/1980 | European Pat. Off. . |
| 73129 | 3/1983 | European Pat. Off. . |
| 0074193 | 3/1983 | European Pat. Off. . |
| 0101563 | 2/1984 | European Pat. Off. . |
| 0110357 | 6/1984 | European Pat. Off. . |
| 0127874 | 12/1984 | European Pat. Off. . |
| 180933 | 5/1986 | European Pat. Off. ............ 502/329 |
| 316399 | 8/1929 | United Kingdom . |
| 582498 | 11/1946 | United Kingdom . |
| 672259 | 5/1952 | United Kingdom . |
| 781405 | 8/1957 | United Kingdom . |
| 1082298 | 9/1967 | United Kingdom . |
| 1159035 | 7/1969 | United Kingdom . |
| 2029719 | 3/1980 | United Kingdom . |
| 1600517 | 10/1981 | United Kingdom . |
| 2076015A | 11/1981 | United Kingdom . |
| 2118061 | 10/1983 | United Kingdom . |

OTHER PUBLICATIONS

Smith et al, Prepr. Pap.-Am. Chem. Soc.-Div Fuel Chem. 29 (5), 269–72, 1984.
World Patent Index Abstract Acc. No. 71-09273S/05 (GB 1,317,304).
Abstract World Patent Indexs Acc. No. 72-59175T/37 (GB 1,335,173).
Abstract World Patent Index Acc. No. 82-51980E/25 (SU 858917).
Abstract World Patent Index Acc. No. 71-60329S/37 (Japan 71/031869).
Abstract World Patent Index Acc. No. 77-36855Y/21 (Japan 50/103496).
Abstract World Patent Index Acc. No. 78-38475A/22 (U.S. 4,186,112).
Abstract World Patent Index Acc. No. 78-82967A/46 (Japan 53/116290).
Abstract World Patent Index Acc. No. 84-257400/42 (European Patent 124744).
Abstract World Patent Index Acc. No. 85-012841/03 (DD 213429).

*Primary Examiner*—Donald B. Moyer
*Assistant Examiner*—Karen E. Kulesza
*Attorney, Agent, or Firm*—Reynold J. Finnegan

[57] ABSTRACT

An improved vapor phase catalytic hydrogenation of aldehydes to the corresponding alcohols wherein the improvement comprises employing a copper oxide-zinc oxide catalyst impregnated with a selectivity enhancer selected from the group consisting of an alkali-metal, transition metal and mixtures thereof.

10 Claims, No Drawings

IMPROVED ALDEHYDE HYDROGENATION PROCESS

This application is a division of prior U.S. application, Ser. No. 926,129, filed Nov. 3, 1986 which is now U.S. Pat. No. 4,762,817.

BACKGROUND OF THE INVENTION

1. Field of the Invention

The present invention relates to the catalytic hydrogenation of aldehydes to alcohols. The present invention specifically pertains to an improved catalyst and a catalytic process for hydrogenating aldehydes to alcohols with a significant improvement in selectivity evidenced by a reduction in the production of undesired by-products. 2. Description of Related Art hydrogenation of aldehydes to produce alcohols has long been practiced. The reaction of an aldehyde with hydrogen generally is carried out in the presence of certain reduced metal compounds which act as hydrogenation catalysts. The commonly used commercial hydrogenation catalysts include copper chromite; cobalt compounds; nickel; nickel compounds which may contain small amounts of chromium or other promoters; mixtures of copper and nickel and/or chromium; and a mixture of reduced copper oxide-zinc oxide (i.e., copper-zinc oxide).

Not surprisingly, all of these hydrogenation catalysts are associated with one or more disadvantages when used for commercially hydrogenating aldehydes to alcohols. Most of these catalysts such as copper chromite, the cobalt compounds, the nickel catalysts and the reduced copper oxide-zinc oxide catalysts, exhibit a less than desired selectivity. Stated otherwise, when hydrogenating aldehydes using such catalysts, the quantity of by-products formed may be higher than desired. Such by-products reduce the desired selectivity of the aldehyde to alcohol conversion and generally must be removed from the hydrogenation product prior to subsequent use of the alcohol. See European Patent Publication Nos. 0 008 767 and 0 074 193. Furthermore, copper chromite catalysts are difficult to prepare and have serious toxicity problems associated with their use, and the cobalt compounds are significantly more costly.

When using nickel catalysts, the principal by-products are ethers and hydrocarbons (paraffins); while the use of reduced copper oxide-zinc oxide catalysts yields esters as the principal by-product. The amount of by-products formed may be anywhere from about 0.5 to about 3.0 weight percent and even higher, based on the total weight of the reaction product.

For example, in the catalytic hydrogenation of butyraldehyde to butanol over a nickel catalyst, a small amount of butyl ether forms; while using a reduced copper oxide-zinc oxide catalyst for the same reaction yields by-product n-butyl butyrate in minor amounts. The ethers form azeotropes with the alcohol hydrogenation products and water frequently present in the product from the feed streams. Thus, a substantial amount of energy is required to separate by-product ethers from alcohols and significant losses of alcohol normally are encountered. For example, separation of butyl ether from butanol required for butanol to pass purity specifications, such as the specification for making acrylates, requires a series of costly distillation steps and because of the butyl ether-butanol azeotrope, four pounds of butanol are lost for every pound of butyl ether formed. Such losses may render the use of an otherwise advantageous hydrogenation catalyst, commercially unattractive.

While by-product esters may be easier to remove, the separation costs and associated losses are not inconsequential. Ester formation leads to a loss of alcohols via the ester stream purged from the bottom of the alcohol refining still in a typical recovery process. The approach used in European Patent Publication No. 0 074 193 to avoid this loss, which involves the recovery and concentration of the esters and then their conversion to additional alcohol by hydrogenolysis in another reactor containing reduced copper oxide-zinc oxide catalyst, requires additional equipment. Furthermore, the amount of esters formed generally increases within increasing temperature in the catalytic hydrogenation reactor. Thus, to minimize by-product ester formation when using reduced copper oxide-zinc oxide catalysts, hydrogenation processes may need to be operated at relatively low temperatures. This is particularly true when an ester such as propyl propionate is the by-product because of the difficulty of separating such esters from the desired alcohol using ordinary distillation techniques. Unfortunately, operation at lower temperatures results in a reduced rate of catalytic hydrogenation.

The tendency of the reduced copper oxide-zinc oxide catalysts to yield higher levels of esters at higher reaction temperatures also complicates the implementation of conventional catalytic techniques. Normally, to compensate for the gradual and unavoidable loss in hydrogenation catalytic activity with time, it is conventional practice to increase reaction temperature with time. When using reduced copper oxide-zinc oxide catalysts, however, such temperature increases lead to an increased formation of ester by-products, thus further complicating subsequent product purification procedures or if the level of by-product ester formation increases above tolerable limits, necessitating an earlier change in the catalyst charge than dictated by hydrogenation rates.

The need to operate the reaction at lower temperatures also complicates the process by requiring either more costly reactors or an increase in the number of adiabatic reaction stages with intercoolers. Furthermore, less useful energy is recovered from the heat of reaction at lower temperatures.

As is evident from the foregoing, a need exists in the art of catalytic hydrogenation of aldehydes to alcohols for a catalyst having improved product selectivity, particularly a catalyst which retains its high selectivity at the high temperatures needed to maximize reaction rates and energy efficiency.

DESCRIPTION OF THE INVENTION

The present invention provides a catalyst and a catalytic process for hydrogenating aldehydes to alcohols which maximizes the production of the desired alcohol product and significantly reduces by-product ester and ether formation relative to prior art catalysts. The present invention is based on the surprising discovery that the addition, to known reduced copper oxide-zinc oxide catalysts, of a small amount of a selectivity enhancer selected from the group consisting of alkali metals, nickel, cobalt and mixtures thereof significantly improves the selectivity of the catalyst by reducing the formation of by-product esters as compared with using a catalyst which does not contain such enhancers. As noted above, by-product ester formation is particularly prevalent during hydrogenation over reduced copper oxide-zinc oxide catalysts at elevated temperatures, which often is preferred to maximize reaction rates and energy efficiency.

The present invention particularly relates to a heterogeneous vapor phase process for producing alcohol by catalytically hydrogenating the corresponding aldehyde over an aldehyde hydrogenation catalyst consisting essentially of a mixture of reduced copper oxide and zinc oxide impregnated with a minor selectivity improving amount of a selectivity enhancer selected from the group consisting of sodium, potassium, lithium, cesium, nickel, cobalt and mixtures thereof.

According to another aspect of the present invention, a preferred aldehyde hydrogenation catalyst composition is provided consisting essentially of a mixture of copper and zinc oxide (i.e., reduced copper oxide-zinc oxide) impregnated with a minor selectivity improving amount of a selectivity enhancer comprising the combination of an alkali metal selectivity enhancer selected from the group consisting of sodium, potassium, lithium, cesium and mixtures thereof, and a transition metal selectivity enhancer selected from the group consisting of nickel, cobalt and mixtures thereof. The present invention also relates to a process for preparing the aldehyde hydrogenation catalyst.

Neglecting other additives, the improved, reduced copper oxide-zinc oxide catalyst of the present invention contains, before reduction, from about 20 to about 70 percent by weight copper oxide and correspondingly from about 80 to about 30 percent by weight zinc oxide. A preferred amount of copper oxide in the pre-reduced or calcined precursor catalyst composition is in the range of about 30 to about 50 weight percent with the balance being zinc oxide; a precursor catalyst composition having a copper oxide to zinc oxide weight ratio in the range of about 1:2 to about 1:1 is particularly preferred.

Aldehyde hydrogenation calcined, precursor catalyst compositions containing a mixture of copper oxide and zinc oxide useful in the present invention may be prepared by any one of a variety of known methods suitable for manufacturing catalytic materials. Thus, an intimate mixture of copper oxide and zinc oxide may be prepared by blending the metal oxide together, for example, by a trituration process or by fusing a mixture of the oxides and then grinding the fused, solidified mass.

Preferably, the mixture is prepared by co-precipitating from an aqueous solution of copper and zinc salts a mixture of copper and zinc compounds which can be easily converted (decomposed) to their oxides, or by the decomposition of a mixture of copper ammine carbonates and zinc ammine carbonates, for example, in the presence of a thermally stabilizing metal oxide such as alumina.

A useful co-precipitation process involves precipitating copper and zinc carbonates from a solution containing soluble copper and zinc salts (e.g. nitrates) in the desired proportion. An oxide mixture then is prepared from the co-precipitated salts using an oxidation treatment, e.g., calcination at an elevated temperature in the presence of oxygen. The calcination product then may be formed into tablets, granules and the like of any suitable size and shape. For example, co-precipitated copper and zinc carbonates are recovered and dried and the dried precipitate is calcined at a temperature within the range of about 550° to 700° F. in the presence of an oxygen-containing gas to convert the carbonates to their oxide form.

Prior to using the catalyst for aldehyde hydrogenation, the catalyst must be reduced by heating it in the presence of a reducing agent such as hydrogen, or carbon monoxide at a temperature in the range of about 150° to 300° C., preferably in the range of about 230° to 260° C. for several hours (e.g. up to about 24 hours). Preferably, a dilute hydrogen stream is used for reducing the catalyst, typically a stream containing one to five percent hydrogen in a gas which is inert to the catalyst during the reduction process such as nitrogen. While nitrogen is the preferred diluent for the reduction gas, other gases also can be used.

It is important to control the catalyst temperature during reduction so that it does not exceed about 300° C., preferably about 260° C., as a consequence of the copper oxide reduction exotherm. Excessive temperatures during reduction contribute to a reduction in catalytic activity. While catalysts may be reduced prior to their use in the aldehyde hydrogenation reaction, catalysts also may be reduced during the process of converting aldehydes to alcohols. Preferably, the mixed oxides are pelleted, extruded or otherwise formed prior to reduction and use, although it is possible to subject the mixed oxide powder to reduction and then form the catalyst composition into the desired shape.

As generally is known, catalyst efficiency depends upon a variety of physical characteristics including surface area and pore volume, which vary widely depending upon how the catalyst is made. The catalyst advantageously has an internal surface area of 30 to 60 square meters per gram. Internal surface area can be determined by the well-known BET method.

In preparing the catalyst by co-precipitation, water soluble mixtures of copper and zinc salts, for example, chlorides, sulfates, nitrates and acetates can be used. It is preferred to employ the nitrates. Normally, co-precipitation is induced by adding an aqueous solution of sodium carbonate to the solution of copper and zinc salts. In standard practice, the precipitated copper and zinc carbonates are washed thoroughly to remove essentially all traces of alkali metal (sodium) nitrate prior to calcination since the prior art indicates that the presence of sodium in the catalyst is undesirable. In this regard, see U.S. Pat. No. 3,303,001 (Col. 2, lines 54–67); U.S. Pat. No. 4,048,196 (Col. 6, line 35–62) and U.S. Pat. No. 4,393,251 (Col. 4, line 35 to Col. 5, line 17). Nonetheless, the prior art has recognized that reduced copper oxide-zinc oxide catalysts made by the standard co-precipitation technique will contain a small amount of sodium. See U.S. Pat. No. 3,303,001 (Col. 4, lines 1–52) and Canadian No. 1,137,519. The prior art, however, has not recognized the advantageous impact of the noted alkali metals, when provided in a selectivity enhancing amount, on the selectivity of reduced copper oxide-zinc oxide catalysts used in aldehyde hydrogenation processes.

Alternatively, the mixture of copper oxide and zinc oxide can be prepared by the simultaneous decomposition of ammine complexes, as for example, soluble copper and zinc tetra-ammine carbonates or soluble copper and zinc di- or tri- ammine carbonates. An aqueous mixture of copper and zinc ammine complexes in the desired copper to zinc weight ratio is heated, e.g., at a temperature in the range of 160° to 210° F., in the presence of a thermally stabilizing metal oxide, such as hydrated alumina and for a sufficient period of time to liberate ammonia and Unreacted carbon dioxide and precipitate the water-insoluble basic carbonates. The resulting slurry then is filtered, and the filter cake calcined. See U.S. Pat. Nos. 3,790,505 and 4,279,781, the disclosures of which are incorporated herein by reference.

Precursor catalyst compositions of copper oxide and zinc oxide suitable for preparing the improved catalyst of the present invention are available commercially. For example, suitable catalyst compositions are available from United Catalyst Inc. under the designations G-66 (See U.S. Pat. No. 3,303,001) and C18HC (See U.S. Pat. No. 3,790,505) and from Katalco under the designation 52-1. While co-precipitation and ammine decomposition are the preferred methods for preparing the catalyst precursor, any method known in the art for forming a mixture of copper oxide and zinc oxide can be used.

In accordance with the present invention, the reduced copper oxide-zinc oxide catalyst or the catalyst precursor is modified by the addition of a minor selectivity improving amount of a selectivity enhancer selected from the group consisting of sodium, potassium, lithium, cesium, nickel and cobalt and mixtures thereof. Within the broad scope of the present invention, the selectivity enhancer can be added to the catalyst composition in a variety of ways, all of which are encompassed by the term "impregnating" used in the specification and claims.

For example, the selectivity enhancer may be impregnated or incorporated initially into the precursor catalyst composition when it is prepared by adding the selectivity enhancer, e.g. as a water-soluble salt of the selectivity enhancer, to the solution from which the copper oxide and zinc oxide precursor compounds, e.g., copper and zinc carbonates, are co-precipitated. The selectivity enhancer could be co-precipitated with the copper and zinc salts or a residue of the selectivity enhancer could be distributed over the precipitated copper and zinc salts when the precipitated salts are dried. Alternatively, the selectivity enhancer(s) could be mixed with or impregnated on the co-precipitated copper and zinc salts, after they are recovered and either before or after drying. The treated composition then is calcined to convert the precipitated or impregnated selectivity enhancer salt to its oxide form along with the copper and zinc salts.

The selectivity enhancer(s) also could be added to the catalyst precursor, i.e., to the mixture of copper oxide and zinc oxide. For example, the calcined catalyst precursor, preferably as a powder or as received from a commercial catalyst supplier, could be wet with an aqueous solution of a selectivity enhancer, dried and then calcined to convert the selectivity enhancer salt to its oxide form. Depending on the particular selectivity enhancer used and its form, as is indicated below, calcination of the treated catalyst precursor also might be avoided in some circumstances. In yet an additional alternative, useful in those circumstances where calcination of the selectivity enhancer residue is unnecessary, the selectivity enhancer could be added directly to the reduced copper oxide-zinc oxide catalyst. Preferably, the selectivity enhancer is incorporated into the catalyst by impregnating a catalyst precursor composition with an aqueous solution of the selectivity enhancer. For example, an aqueous slurry of the powdered catalyst precursor composition and the selectivity enhancer can be spray dried to form a powder suitable for forming catalyst pellets. Better control of the amount of selectivity enhancer added to the catalyst and the uniformity of the dispersion of the selectivity enhancer in the catalyst can be obtained using this technique.

Alkali metal selectivity enhancers may be introduced into the catalyst as a hdyroxide or as any salt which upon calcination yields the alkali metal oxide. One suitable alkali metal salt used for impregnating the catalyst is the readily available and water soluble nitrates. Alkali metal selectivity enhancers also can be added as their carbonates, and bicarbonates. Standard calcination procedures can be used to convert the alkali metal compounds to their oxide form. On subsequent reduction of the catalyst precursor, the alakli metal oxides are converted to alkali metal hydroxides. Other alkali metal compounds suitable for impregnating catalysts for use in the present invention will be apparent to those skilled in the art.

While not wishing to be bound to any particular explanation, applicants believe that the alkali metal selectivity enhancers are present in the catalyst in their hydroxide or hydrated oxide form. Consequently, an alkali metal can be introduced into the catalyst precursor or into the calcined or reduced catalyst using an alkali metal hydroxide. In this later case, a mild drying step suffices instead of calcination for catalyst preparation.

The alkali metal selectivity enhancer(s) is added to the catalyst in a selectivity improving amount, (based on the precursor catalyst composition of copper oxide and zinc oxide) of between about 0.05 and 7.0 weight percent, preferably between about 0.5 and 3.5 weight percent (on a free total alkali metal basis). Generally, the activity of the catalyst decreases as the level of alkali metal addition is increased toward its upper limit. Moreover, catalysts impregnated with certain alkali metals, such as sodium, may exhibit a lower activity than catalysts impregnated with a similar amount of another alkali metal such as potassium. Thus, in such circumstances a lower level of the sodium additive should be used. Actual catalyst activities can be determined using routine experimentation.

Preferably, the alkali metal is potassium and it can be added to a copper oxide-zinc oxide catalyst precursor in the form of potassium hydroxide or a decomposible salt such as potassium carbonate, potassium bicarbonate or potassium nitrate. Upon calcining the precursor catalyst composition, the decomposible alkali metal salt is converted to its oxide form. For example, in the case of potassium carbonate, it is thought that potassium oxide is formed on calcination. When the catalyst is subsequently reduced using hydrogen, the oxide likely is converted to its hydroxide form by reaction with water released during the hdyrogen-copper oxide reduction reaction.

As noted, the transition metals nickel and cobalt also are selectivity enhancers in accordance with the present invention. Again, to provide a nickel or cobalt enhanced catalyst a variety of impregnation procedures can be used. Generally, these transition metals are impregnated on the catalyst by immersing the precursor catalyst composition and preferably the calcined precursor catalyst composition, as a powder or as preformed tablets or granules, in an aqueous salt solution of nickel or cobalt and then drying the catalyst. The salt used should form nickel oxide or cobalt oxide upon calcination. For example, an aqueous slurry of the catalyst precursor composition and nickel nitrate can be spray dried to a powder, followed by calcination at about 700° F. The nickel or cobalt selectivity enhancer also could be added to the catalyst by including a small amount of an appropriate water soluble salt in the original copper and zinc salt solution undergoing co-precipitation. Other ways of impregnating the catalyst with nickel and cobalt also will be apparent to those skilled in the art.

It has been found that to be most effective these transition metals should be lightly impregnated on the reduced copper oxide-zinc oxide catalyst. Typically the nickel or cobalt salt should be applied at a sufficient level to provide a selectivity improving amount of no more than about 0.5 to about 5.0 weight percent nickel and/or cobalt based on the weight of the calcined precursor catalyst composition, preferably between about 1 weight percent to about 4 weight percent. By using this low amount of nickel and cobalt selectivity enhancers, the modified, reduced copper oxide-zinc oxide catalyst avoids the undesirable ether and paraffin-forming tendency of primarily nickel or cobalt catalysts.

A particularly preferred aspect of the present invention comprises a reduced copper oxide-zinc oxide catalyst which has been impregnated with both an alkali metal selectively enhancer and a transition metal selectively enhancer. This use of a combination of selectivity enhancers has been found to yield a catalyst composition which, when used as the hydrogenation catalyst for converting aldehydes to alcohols, exhibits a synergistic reduction in by-product ester formation and continues to exhibit essentially no ether or paraffin forming tendencies. Furthermore, the greatest benefit of this improved catalyst composition is observed at higher temperature reaction conditions and at increased residence times (i.e. low space velocities), conditions under which commercial reduced copper oxide-zinc oxide experience a significant degradation in selectivity.

When used in combination, the alkali metal, preferably potassium, should be included in the catalyst composition is an amount between about 0.05 to 7.0 weight percent (based on weight percent of free alkali metal in the calcined precursor catalyst composition), and preferably in an amount between 0.3 and 3.5 weight percent; while the transition metal, nickel and/or cobalt, is present in an amount between about 0.5 weight percent to about 5.0 weight percent (based on the weight of the calcined precursor catalyst composition) and preferably in an amount between 1.0 and 4.0 weight percent. A particularly preferred catalyst composition contains about 0.6 weight percent potassium and about 1.5 to 2.5 weight percent nickel.

Although not wishing to be bound by any particular theory, applicants believe that by adding the nickel or cobalt transition metal selectivity enhancer to an alkali metal containing catalyst, ester formation due to two different reaction mechanisms both are suppressed. At high residence times, the outlet portion of a hydrogenation reaction contains primarily alcohol and it is believed that ester formation in the vicinity of the reactor outlet involves the formation of a hemiacetal from an aldehyde and an alcohol followed by dehydrogenation of the hemiacetal to an ester. On the other hand, it also is known that an ester can be formed according to the well-known Tischenko reaction from two aldehyde molecules. It is postulated that this reaction occurs near the inlet of the reactor where the concentration of aldehyde is highest. Apparently, the nickel or cobalt transition metal-selectivity enhancer is best able to suppress the first ester-formation mechanism occurring near the reactor outlet, while alkali metal selectivity enhancer impregnation appears to be most effective on the latter ether-formation mechanism which predominates near the reactor inlet.

While the present catalyst can be used in an unsupported form, it also may contain an inert support or a binder such as alumina, pumice, graphite, silicon carbide, zirconia, titania, silica, alumina-silica, chromina, and the inorganic phosphates, silicates, aluminates, borates, and the like which are stable under conditions to which the catalysts will be subjected and do not adversely affect the activity or selectivity of the catalyst. Calcium oxide-containing cements used to impart strength or structure to catalysts also may be used.

The catalytic process of the present invention can be used for hydrogenating a wide variety of straight or branched chain, saturated or unsaturated aldehydes containing from 2 to 22 carbon atoms. The aldehyde reactants also may contain other oxygenated groups except carboxylic acid groups. The feed stock is limited primarily, only by the practicability of vaporizing higher boiling aldehydes. Suitable aldehydes include saturated aldehydes like acetaldehyde, propionaldehyde, iso-butyraldehyde, n-butyraldehyde, isopentyl aldehyde, 2-methylpentaldehyde, 2-ethylhexaldehyde, 2-ethylbutyraldehyde, n-valeraldehyde, iso-valeraldehyde, caproaldehyde, methyl-n-propylacetaldehyde, iso-hexaldehyde, caprylaldehyde, n-nonylaldehyde, n-decanal, dodecanal, tridecanal, myristic aldehyde, pentadecaldehyde, palmitic aldehyde, stearic aldehyde and such unsaturated aldehydes as acrolein, methacrolein, ethacrolein, 2-ethyl-3-propylacrolein, crotonaldehyde and the like. The aldehyde may be in a substantially pure state or mixed with a component or components other than the aldehyde itself. Further, a mixture of aldehydes may be employed.

The aldehyde or mixture of aldehydes employed may be obtained by an oxo process. Either a portion or all of the product mixture of an oxo process, i.e., the reaction of olefins with carbon monoxide and hydrogen in the presence of a catalyst to add a carbonyl group at one of the carbon atoms of the olefinic group, can be used. Of course, the aldehyde or mixture of aldehydes can be obtained by processes other than the oxo process such as by oxidation of olefins or saturated hydrocarbons or by an aldol condensation. The present invention is not limited to the source of any particular aldehyde.

The aldehyde in a vaporous state is brought into contact with the hydrogenation catalyst in the presence of a hdyrogen-containing gas. While substantially pure hydrogen alone can be used, it is preferable in some cases to provide the hydrogen in admixture with other gases, desirably inert to the aldehyde and catalyst. Suitable inert gases for mixing with hydrogen are nitrogen and methane. The term "hydrogen-containing gas" includes both substantially pure hydrogen gas as well as gaseous mixtures containing hydrogen.

While the concentration of hydrogen in the reaction zone is not critical, there generally should be an excess of hydrogen over the stoihiometric requirement relative to the aldehyde to be reduced. Generally, the mol ratio of hydrogen to aldehyde will be from about 5 to 400 and preferably from about 10 to 200. For aldehydes containing from about 2 to 8 carbon atoms, the mol ratio of hydrogen to aldehyde preferably is in the range of about 10 to 30.

Normally, the hydrogenation reaction is conducted at a temperature of at least about 100° C. and because of the high selectivity of the present catalyst can be conducted at a temperature as high as about 300° C. Preferably, the reaction is carried out at a temperature in the range of about 120° to 260° C. This temperature range balances the competing factors of energy and reaction rate. The reaction can be conducted at any suitable pressure from atmospheric up to about 600 psig. In view of the need to maintain the aldehyde and alcohol products in the vaporous state, above the due point, reaction pressure is somewhat influenced by reaction temperature, the aldehyde undergoing hydrogenation and the quantity of hdyrogen-containing gas. Space velocities for the hydrogenation reaction may range from about 0.1 to 2.0 based on the liquid volume of aldehyde fed to the vaporizer per volume of catalyst per hour.

The process of the present invention preferably is carried out in a continuous manner. In the preferred method of continuous operation, the aldehyde, the mixture of aldehydes, or the oxo reaction products are vaporized as needed and brought together with the hydrogen-containing gas at the desired temperature and pressure over the catalyst of the present invention. The catalyst advantageously may be used in a fixed catalyst bed reactor. The reaction zone may be an elongated tubular reactor with the catalyst supported within the tubes. Adiabatic tank type reactors also can be used. In such reactors the heat of reaction causes an increase in reaction temperature from reactor inlet to reactor outlet.

The selectivity enhanced catalysts of the present invention, and particularly those enhanced with both alkali metal and transition metal selectivity enhancers, are able to suppress ester formation at high temperatures and high alcohol concentrations. Thus, adiabatic reactors can be used to their fullest potential. The catalyst also may be used, however, in an isothermal or nearisothermal reactor wherein the catalyst is contained in cooled tubes or cooling tubes are placed within a fixed bed of catalyst. As noted above, good selectivity can be obtained even using catalysts of the present invention when the entire catalyst bed is operated near its maximum temperature. Under such conditions, the heat of reaction can be recovered as useful energy, such as for example by generating high pressure steam.

Alcohol product recovered from the hydrogenation reaction is separated from Unreacted hydrogen by condensation and excess hydrogen is recompressed and recycled to the reaction zone. The crude alcohol product can be used as is, or can be further purified using conventional techniques such as fractional distillation. Unreacted aldehyde which may be recovered also can be recycled.

The following examples are presented to illustrate the present invention and are not intended to constitute a limitation on its scope which is defined in the appended claims.

Catalyst Preparation

A solution (16 liters) containing 417 grams of copper, supplied as copper nitrate, and 858 grams of zinc, supplied as zinc nitrate, is heated to about 110° F. and sprayed into a 15.7 weight percent sodium carbonate solution (12.75 liters) which is mechanically agitated and maintained at about 140° F. The final pH of the precipitation mixture is about 7.0 to 8.5. After precipitation, the copper-zinc basic carbonate is washed to remove sodium by decanting off approximately 80 percent of the filtrate. Four washes and decantations using 100° to 120° F. wash water are used to lower the sodium content in the calcined filter cake to about 0.1 to 0.15 weight percent. Calcination of the copper-zinc basic carbonate precipitate yields a mixture of copper oxide and zinc oxide (catalyst precursor composition). An aqueous slurry (30 weight percent solids) of the catalyst precursor, graphite, nickel nitrate and potassium nitrate in sufficient amounts to provide a calcined catalyst composition of about 0.7 weight percent potassium oxide, 3.0 weight percent nickel oxide, 2.0 weight percent graphite, 32.0 weight percent copper oxide and 62.3 weight percent zinc oxide is then spray dried. The spray dried powder is tabbleted and then calcined at 700° F. to decompose the nitrates. Subsequent reduction yields a catalyst according to the present invention.

EXAMPLE 1

Mixed butyraldehyde containing one part isobutyraldehyde and nine parts n-butyraldehyde, as produced in a low pressure hydroformylation reaction of propylene over a rhodium-containing catalyst was divided in equal portions and separately fed to the reactors in a two stage adiabatic pilot plant scale hydrogenation reactor system at a space velocity of 0.8 (volumes of total liquid feed to total volume of catalyst per hour). A gas feed containing 60% hydrogen and 40% nitrogen was fed to the inlet of the first reactor at a mol ratio of hydrogen to aldehyde of 13 to one. Gas effluent from the first reactor was mixed with a second portion of mixed butyraldehyde feed and was passed into the second reactor in series. A pressure of 100 psig was maintained at the outlet of the second reactor. The vaporized aldehyde and hydrogen mixture was fed to the first reactor at 125° C. and exited the reactor at a temperature of 201° C. The effluent from the first reactor, after adding the additional aldehyde, was adjusted to 128° C. at the inlet to the second reactor and exited the second reactor at a temperature of 196° C. The catalyst in both reactors was prepared by reducing a calcined catalyst precursor composition consisting essentially of about 33 weight percent copper oxide and about 67 weight percent zinc oxide which had been impregnated with about 3% by wt. nickel oxide (about 2.4% by wt. nickel) and about 1% by wt. potassium carbonate (about 0.6% by wt. potassium). The calcined precursor catalyst composition was reduced with a dilute hydrogen stream containing nitrogen as a diluent at a temperature near 200° C. The mixed butanol product condensed from the outlet of the second reactor contained 1.6 wt. % Unreacted aldehyde and only 0.05 wt. % mixed iso-and n-butyl butyrates.

EXAMPLE 2

In a comparative example to Example 1, an experiment was run in the same pilot plant equipment described in Example 1 at similar reaction conditions except that the catalyst was a nonmodified, reduced copper oxide-zinc oxide catalyst (precursor catalyst of about 33 weight percent copper oxide and about 67 weight percent zinc oxide). The product condensed from the outlet of the second reactor contained 0.3% aldehyde and 2.9% mixed butyl butyrates, representing a significant increase in the production of ester by-product. In another experiment at a 188° C. peak temperature, a product sample was recovered which contained 1.9% unreacted aldehyde and 1.2% butyl butyrate.

Both experiments yielded significantly more ester than obtained with the catalyst in Example 1.

EXAMPLE 3

Propionaldehyde was fed to a steam jacketed tubular reactor one-half inch in diameter by four feet in length filled with the selectivity enhanced catalyst described in Example 1. During the test, liquid hourly space velocity was maintained at 0.4, temperature was near isothermal at 150° C., pressure was fixed at 50 psig and pure hydrogen was fed as the co-reactant at a 20 to 1 mol ratio of hydrogen to propionaldehyde. The condensed product contained only 0.02 wt. % propyl propionate and 0.04 wt. % propionaldehyde.

EXAMPLE 4

Valeraldehyde was fed to a small laboratory tubular reactor operated isothermally at 150° C. and 60 psig. The same selectivity enhanced catalyst used in Example 1 was employed. At 95% aldehyde conversion, the production of by-product pentyl pentanoate was only 0.08 wt. %.

EXAMPLE 5

The impact on aldehyde hydrogenation of various modifications made to calcined precursor catalyst compositions consisting essentially of about 33% copper oxide and about 67% zinc oxide catalyst before reduction were examined in this Example. hydrogenation tests were run in a set of small laboratory tubular reactors operated under identical conditions. The results of the test are contained in the following table. Reaction conditions were: pressure - 60 psig, outlet temperature - 192° C., feed mol ratio - 11 to 1 hydrogen to butyraldehyde, and space velocity (based on gas flow at standard conditions) 120,000 volumes of total gas per volume of catalyst per hour.

| | Test No. | | | | |
|---|---|---|---|---|---|
| Modifier: | 5A none | 5B 3% NiO | 5C 3% CoO | 5D 1% $K_2CO_3$ | 5E 1% $K_2CO_3$ +3% NiO |
| Aldehyde Converted % | 76 | 77 | 72 | 79 | 70 |
| Butyl Butyrate % | 0.50 | 0.18 | 0.13 | 0.13 | 0.05 |

(no significant amounts of butyl ether or propane were formed) (1% $K_2CO_3$ corresponds to 0.6% potassium)

As shown, use of a nickel, cobalt or potassium enhanced catalyst leads to a significant decrease in the production of the ester by-product. An order of magnitude reduction was obtained using a combination of potassium and nickel selectivity enhancers.

EXAMPLE 6

Comparative data at high conversions of over 99% were obtained with selectivity enhanced and non-enhanced reduced copper-zinc oxide catalysts in reactors fed a mixture of iso- and nbutyraldehydes in a 1 to 9 weight ratio. Peak reaction temperatures were about 210° C. Inlet conditions were adjusted to obtain a partial pressure of 6 psia for the butyraldehydes and of 70 to 77 psia for hydrogen. The total gaseous feed rate was 4800 standard cubic feet per cubic feet of catalyst per hour. Results are tabulated below.

| | Test No. | | |
|---|---|---|---|
| Modification: | 6A none | 6B 1% $K_2CO_3$ | 6C 1% $K_2CO_3$ + 3% NiO |
| Total iso and normal butyl butyrates (%) | 2.71 | 0.55 | 0.05 |

As in Example 5, while use of an alkali metal selectivity enhancer alone significantly reduced the production of by-product ester by about 80%, the combination of potassium and nickel resulted in an additional order of magnitude decrease.

EXAMPLE 7

Using the reactors and reaction conditions described in Example 5 tests were conducted contrasting the performance of various copper containing catalysts. The catalysts tested, as reported below, were not effective in substantially reducing the amount of ester formation or the formation of other by-products such as ethers. Results are presented in the following table.

| Calcined Precursor Catalyst composition (before reduction) | % ester | % ester | % alcohol |
|---|---|---|---|
| Mixed CuO + NiO + CoO | 0.15 | 1.63 | 77 |
| CuO + ZnO + 5%CaO | 0.50 | 0 | 81 |
| CuO + ZnO + 10%NiO | 0.48 | 0 | 83 |

While certain specific embodiments of the invention have been described with particularity herein, it will be recognized that various modifications thereof will occur to those skilled in the art. Therefore, the scope of the invention is to be limited solely by the scope of the appended claims:

We claim:

1. In a heterogenous vapor phase process for producing an alcohol by contacting a mixture of a vaporous stream of the corresponding aldehyde and a hydrogen-containing gas with a solid hydrogenation catalyst the improvement comprising employing as said hydrogenation catalyst a reduced precursor catalyst composition which consists essentially of a mixture of reduced copper oxide-zinc oxide impregnated with a selectivity improving amount of a selectivity enhancer selected from the group consisting of
    (a) potassium in an amount of between about 0.5 and 3.5 percent by weight based on the weight of copper oxide and zinc oxide in the precursor catalyst composition before its reduction;
    (b) a transition metal selectivity enhancer selected from the group consisting of nickel, cobalt and mixtures thereof in the amount of between about 0.5 and 5.0 percent by weight based on the weight of copper oxide and zinc oxide in the precursor catalyst composition before its reduction; and
    (c) a selectivity enhancer comprising the combination of
        (i) an alkali metal selectivity enhancer selected from the group consisting of sodium, potassium, lithium, cesium, and mixtures thereof, in an amount of between about 0.05 and 7.0 percent by weight based on the weight of copper oxide and zinc oxide in said precursor catalyst composition before its reduction; and (ii) a transition metal selectivity enhancer selected from the group consisting of nickel, cobalt, and mixtures thereof, in an amount of between about 0.5 and 5.0 percent by weight based on the weight of copper oxide and zinc oxide in the precursor catalyst composition before its reduction.

2. The process of claim 1 wherein said selectivity enhancer is potassium and the amount of said potassium is about 0.6 percent by weight.

3. The process of claim 1 wherein said selectivity enhancer is a transition metal selected from the group consisting of nickel, cobalt, and mixtures thereof.

4. The process of claim 3 wherein said amount is between about 1.0 and 4.0 percent by weight.

5. The process of claim 3 wherein said selectivity enhancer is nickel.

6. The process of claim 1 wherein said selectivity enhancer comprises the combination of (i) an alkali metal selectivity enhancer selected from the group consisting of sodium, potassium, lithium, cesium and mixtures thereof, and (ii) a transition metal selectivity enhancer selected from the group consisting of nickel, cobalt, and mixtures thereof.

7. The process of claim 6 wherein said selectivity enhancer comprises the combination of (i) potassium in an amount between about 0.3 and 3.5 weight percent, and, (ii) nickel in an amount between about 1.0 and 4.0 weight percent.

8. The process of claim 6, wherein the amount of alkali metal selectivity enhancer is between about 0.3 and 3.5 weight percent and the amount of transition metal selectivity enhancer is between about 1.0 and 4.0 weight percent.

9. The process of claim 7, wherein the amount of potassium is about 0.6 weight percent and the amount of nickel is between 1.5 and 2.5 weight percent.

10. The process as defined in claim 9, wherein the amount of nickel is about 2.4 weight percent.

* * * * *